US010591885B2

(12) United States Patent
Gluck et al.

(10) Patent No.: US 10,591,885 B2
(45) Date of Patent: Mar. 17, 2020

(54) DEVICE CONTROL BASED ON A USER'S PHYSICAL SETTING

(71) Applicant: International Business Machines Corporation, Armonk, NY (US)

(72) Inventors: Olympia Gluck, Haifa (IL); Itzhack Goldberg, Hadera (IL); Jinho Hwang, Ossining, NY (US); Maja Vukovic, New York, NY (US); Yelena Zilberstein, Yoqneam Ilint (IL)

(73) Assignee: International Business Machines Corporation, Armonk, NY (US)

( * ) Notice: Subject to any disclaimer, the term of this patent is extended or adjusted under 35 U.S.C. 154(b) by 227 days.

(21) Appl. No.: 15/702,847

(22) Filed: Sep. 13, 2017

(65) Prior Publication Data

US 2019/0079481 A1    Mar. 14, 2019

(51) Int. Cl.
| G05B 19/048 | (2006.01) |
| G05D 1/00 | (2006.01) |
| G05D 1/02 | (2006.01) |
| A61B 5/11 | (2006.01) |
| A61B 5/16 | (2006.01) |
| H04L 29/08 | (2006.01) |
| G06N 5/02 | (2006.01) |
| G06N 20/00 | (2019.01) |

(52) U.S. Cl.
CPC .......... *G05B 19/048* (2013.01); *A61B 5/1118* (2013.01); *A61B 5/165* (2013.01); *G05D 1/0088* (2013.01); *G05D 1/0221* (2013.01); *H04L 67/12* (2013.01); *H04L 67/22* (2013.01); *A61B 2503/12* (2013.01); *A61B 2560/0242* (2013.01);

(Continued)

(58) Field of Classification Search
CPC .............. G05B 19/048; G05B 15/02; G05B 2219/24015; G05D 1/0221; G05D 1/0088; G05D 2201/0213; A61B 5/1118; A61B 5/165; A61B 2503/12; A61B 2560/0242;

(Continued)

(56) References Cited

U.S. PATENT DOCUMENTS 8,682,485 B2 *  3/2014  Anhalt ................... B25J 9/163
                                                                     700/246
9,747,277 B2 *  8/2017  Cecchi ............... G06F 17/2765

(Continued)

FOREIGN PATENT DOCUMENTS

WO  2012112695 A1  8/2012
WO  2015127361 A1  8/2015

OTHER PUBLICATIONS

P. Mell et al., "The NIST Definition of Cloud Computing", National Institute of Standards and Technology, Information Technology Laboratory, Sep. 2011, pp. 1-7.

(Continued)

*Primary Examiner* — Nicholas Kiswanto
(74) *Attorney, Agent, or Firm* — Law Office of Jim Boice

(57) ABSTRACT

A processor-implemented method controls a self-driving vehicle (SDV). One or more processors receive, from one or more physical sensors, physical state readings that describe a physical environment of multiple persons that are in spatial proximity with one another. The processors determine, based on the physical state readings, a context of a physical setting of the multiple persons. The processors identify, based on the context of the physical setting of the multiple persons, an SDV that is known to modify a state of the multiple persons. The processor(s) then transmit, to a device controller, a device activation signal to activate the SDV, in order to transport cargo that one of the multiple persons was previously scheduled to transport.

12 Claims, 6 Drawing Sheets

(52) U.S. Cl.
CPC .............. *G05B 2219/24015* (2013.01); *G05D 2201/0213* (2013.01); *G06N 5/02* (2013.01); *G06N 20/00* (2019.01); *H04L 67/306* (2013.01)

(58) Field of Classification Search
CPC ....... H04L 67/12; H04L 67/22; H04L 67/306; G06N 20/00; G06N 5/02
See application file for complete search history.

(56) References Cited

U.S. PATENT DOCUMENTS

| | | | |
|---|---|---|---|
| 2004/0210159 A1* | 10/2004 | Kibar .................. | A61B 5/4803 600/558 |
| 2015/0110277 A1 | 4/2015 | Pidgeon et al. | |
| 2015/0356412 A1 | 12/2015 | Faith et al. | |
| 2017/0091662 A1 | 3/2017 | Sanchez et al. | |
| 2017/0341746 A1* | 11/2017 | Erickson .............. | B64C 39/024 |

OTHER PUBLICATIONS

Pamela Trevithick, "Effective Relationship-Based Practice: A Theoretical Exploration". Journal of Social Work Practice, vol. 17, No. 2, 2003, pp. 163-176.
Klein et al., "Computers That Recognize and Respond to User Emotion: Theoretical and Practical Implications". MIT Media Lab Tech Report 538 to Appear in Interacting With Computers, 2001.
Anonymous, "Improved Customer Service With Appeasement Offers Based on Cognitive Insights". IPCOM000250095D, May 31, 2017.
Anonymous, "Method and Apparatus for Intentional Cognitive Engagement Extender". IPCOM000247821D, Oct. 6, 2016.

* cited by examiner

DEVICE CONTROL BASED ON A USER'S PHYSICAL SETTING

BACKGROUND

The present invention relates to the field of devices, and particularly to the selective control of devices. Still more particularly, the present invention relates to controlling devices by a cognitive mediator system that selectively controls the devices based on cognitive states of users of the devices.

SUMMARY

In one or more embodiments of the present invention, a processor-implemented method controls a self-driving vehicle (SDV). One or more processors receive, from one or more physical sensors, physical state readings that describe a physical environment of multiple persons that are in spatial proximity with one another. The processors determine, based on the physical state readings that describe the physical environment of the multiple persons that are in spatial proximity with one another, a context for the multiple persons that are in spatial proximity with one another, where the context describes a physical setting in which the multiple persons are located. The processors identify, based on the context that describes the physical setting in which the multiple persons are located an SDV that is known to modify a state of the multiple persons. The processor(s) then transmit, to a device controller, a device activation signal to activate the SDV, such that the device activation signal directs the SDV to transport cargo that one of the multiple persons was previously scheduled to transport. The device activation signal is transmitted to the SDV via a user communication device, which is in wireless communication with the device controller, and which wirelessly transmits the device activation signal to the device controller in response to the user communication device coming within a predefined distance of the device controller. The device controller is inactive until the user communication device is within the predefined distance of the device controller.

The described invention may also be implemented in a computer system and/or as a computer program product.

DETAILED DESCRIPTION

Figure 1:
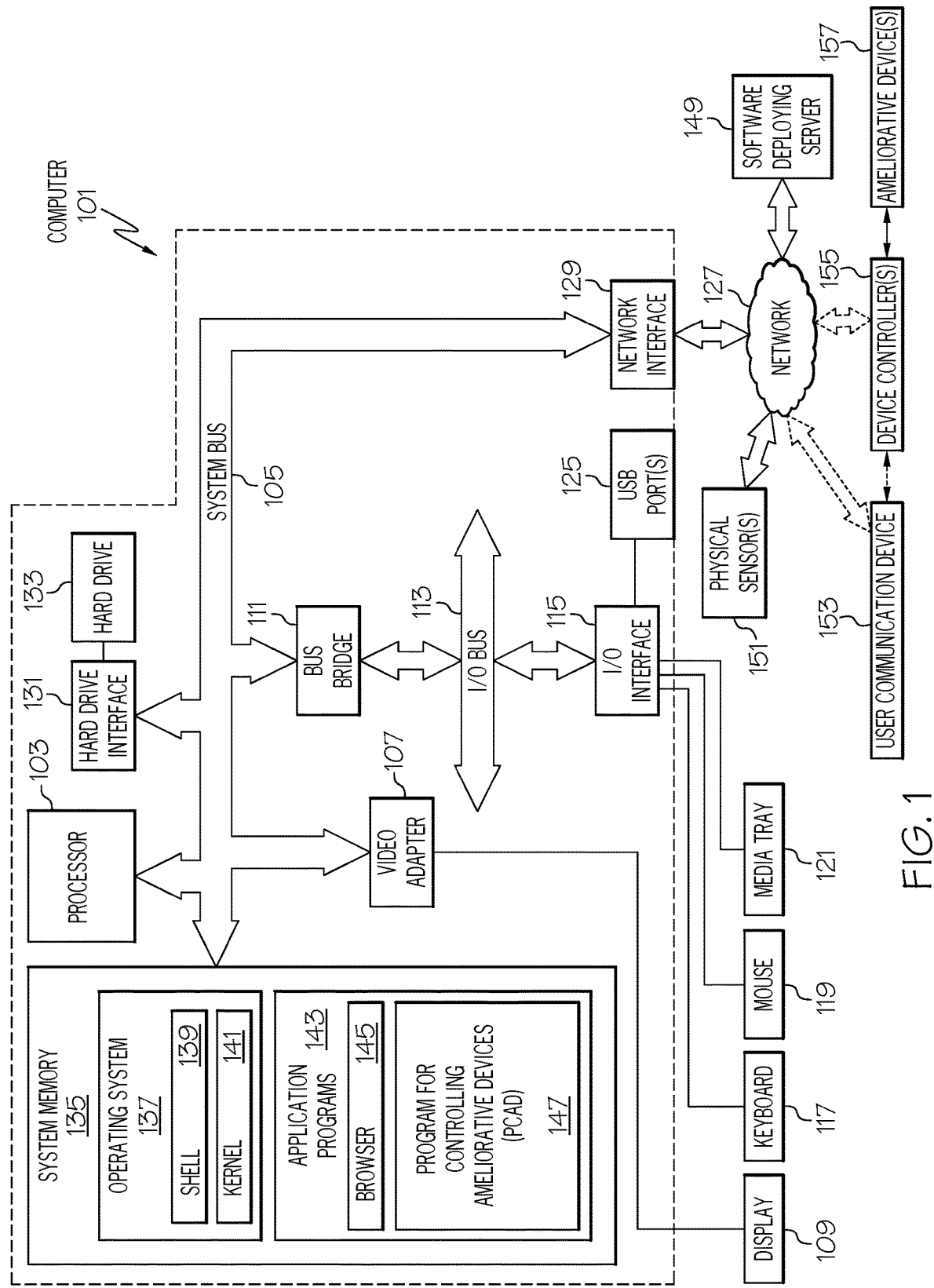
FIG. 1 depicts an exemplary system and network in which the present disclosure may be implemented.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Hash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Interpersonal friction between persons is unfortunately commonplace, since persons are often unable to control their tempers or to seek consolatory services to help them reconcile their differences. As such, simple arguments get out of hand and escalate into more severe conflicts.

Thus, one or more embodiments of the present invention utilize a cognitive mediator system that detects and/or predicts an argument/conflict, and intervenes by activating one or more ameliorative devices that are known to reduce the tensions that are causing the argument/conflict.

In one or more embodiments, the present invention utilizes an autonomous learning agent that uses its knowledge to recognize problematic situations early on, and then to intervene either by engaging itself as a mediator or soliciting help from another entity.

Thus, in one or more embodiments, the present invention utilizes a cognitive mediator system that monitors physical sensors where two or more persons (or alternatively, only one person) are located. These physical sensors are able to identify the state of the location (e.g., the air temperature, sound levels, etc.) and/or the state of the persons (e.g., their emotional state, movement, speech, etc.).

The cognitive mediator system thus infers a cognitive state S of a user or couple or group of users (e.g. distressed, tired, teething, in pain, upset, etc.), a context C of the users (e.g. a meeting, family setting, yelling, quiet, crying), and an activity pattern P (including new behaviors) of the users, where S, C, and P are all based on data provided by the sensors in the environment that show the time of day, the temperature and humidity of the room, the social setting, any crying, speech, conversations, and vocalization patterns of the persons in the room.

The cognitive mediator system then generates/triggers appropriate useful amelioration actions, such as activating devices that play soothing music, lower lighting levels, reduce room temperatures, etc. based on {S, C, P}.

In an embodiment of the present invention, the cognitive mediator system is equipped with a decision module that is configured with a rule-based heuristic engine, custom learning models (e.g., that use natural language processing (NLP) based artificial intelligence), or a combination thereof to determine actions based on user profile(s) and settings. That is, the cognitive mediator system is able to learn about the profiles of the user(s) (e.g., how they react to certain calming devices, etc.). Based on these profiles and the level of interpersonal hostility that is deemed acceptable by the system (the "settings"), the system will deploy/activate the appropriate ameliorative devices accordingly.

In an embodiment of the present invention, the cognitive mediator system understands the history of people involved in the dispute, so that the context or characteristics of each person is recorded in the system to be used when making judgements or decisions regarding which, if any, ameliorative devices are activated. In one or more embodiments, the present invention employs techniques such as a number-theoretic transform (NTT) algorithm to predict the context, state, conversation flow, etc., of the persons involved, in order to preempt escalations in the conflict by the use/activation of devices and the use of machine learning algorithms (e.g., a support vector machine) to initiate the appropriate actions to ameliorate the situations.

Based on the ameliorating actions, one or more ameliorative devices may be configured (e.g., turning the volume up/down on a music player, playing a certain tone, playing a particular video, etc.) to help soothe the situation.

In an embodiment of the present invention, the system described herein is an OPT IN system, so that users elect to use the system and/or to share their personal data needed to train and/or control the cognitive mediator system described herein.

As described herein, the cognitive mediator system is connected to an Internet of Things (IoT) made of communicative devices (i.e., smart home/office devices, wearables, mobile devices, speakers, etc.) and sensors. The cognitive mediator system uses those devices to create ameliorating actions based on the diagnosed situations. For example, when the system detects that people in the room or office feel hot, it automatically turns on the air conditioner or fan to lower the temperature. If an argument between these persons escalates, distractions such as music, an announcement, etc. are used to ease the situation.

In an exemplary embodiment of the present invention, the following learning algorithm classifies actions based on collected information from physical sensors:

---

Inputs: Labeled set $D_l$, unlabeled set $D_u$, number of steps T, number of examples per iteration S
t=1;
while t <= T do
    Train a multi-label SVM classifier f based on training data $D_l$
    For each instance x in $D_u$ do
        Predict its label vector y using the LR (loss reduction)-based prediction method $$D_s^* = \mathrm{argmax}_{Ds}\left(\sum_{X \in Ds}\sum_{i=1}\left(\frac{1 - y^i f_i(x)}{2}\right)\right)$$

constrained to $y^i \in \{-1,1\}$
        (equation for Maximum loss reduction with maximal confidence)
        Calculate the expected loss reduction with the most confident label vector y, $$\mathrm{Score}(x) = \sum_{i=1}^{k}\left(\frac{1 - y^i f_i(x)}{2}\right)$$

Sort score(x) in decreasing order for all x in $D_u$
        Select a set of S examples $D_s^*$ with the largest scores (or experienced SME input),
            and update the training set $D_l < -D_l + D_s^*$
    end for
Train the multi-label learner 1 with $D_l$
t= t+1;
end while
such that $f_i(x)$ is a SVM classifier associated with class i;
$x^1 \ldots x^n$ data points (e.g. feature vector for patterns - [time, location, mood emotion, surroundings, education level, memory metrics, cognitive states, activity patterns, etc.]; and
Output is action steps taken to resolve the situation.

---

With reference now to the figures, and in particular to FIG. 1, there is depicted a block diagram of an exemplary system and network that may be utilized by and/or in the implementation of the present invention. Some or all of the exemplary architecture, including both depicted hardware and software, shown for and within computer 101 may be utilized by software deploying server 149 and/or physical sensor(s) 151 and/or user communication device 153 and/or device controller(s) 155 and/or ameliorative device(s) 157 shown in FIG. 1.

Exemplary computer 101 includes a processor 103 that is coupled to a system bus 105. Processor 103 may utilize one or more processors, each of which has one or more processor cores. A video adapter 107, which drives/supports a display 109 (which may be a touch-screen display capable of detecting touch inputs onto the display 109), is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including a keyboard 117, a mouse 119, a media tray 121 (which may include storage devices such as CD-ROM drives, multimedia interfaces, etc.), and external USB port(s) 125. While the format of the ports connected to I/O interface 115 may be any known to those skilled in the art of computer architecture, in one embodiment some or all of these ports are universal serial bus (USB) ports.

As depicted, computer 101 is able to communicate with a software deploying server 149 and/or other devices/systems using a network interface 129. Network interface 129 is a hardware network interface, such as a network interface card (NIC), etc. Network 127 may be an external network such as the Internet, or an internal network such as an Ethernet or a virtual private network (VPN). In one or more embodiments, network 127 is a wireless network, such as a Wi-Fi network, a cellular network, etc.

A hard drive interface 131 is also coupled to system bus 105. Hard drive interface 131 interfaces with a hard drive 133. In one embodiment, hard drive 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, disk management, and mouse and keyboard management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication with software deploying server 149 and other systems.

Application programs 143 in computer 101's system memory (as well as software deploying server 149's system memory) also include a Program for Controlling Ameliorative Devices (PCAD) 147. PCAD 147 includes code for implementing the processes described below, including those described in FIGS. 2-4, and in one or more embodiments for implementing the cloud process described in FIGS. 5-6. In one embodiment, computer 101 is able to download PCAD 147 from software deploying server 149, including in an on-demand basis, wherein the code in PCAD 147 is not downloaded until needed for execution. In one embodiment of the present invention, software deploying server 149 performs all of the functions associated with the present invention (including execution of PCAD 147), thus freeing computer 101 from having to use its own internal computing resources to execute PCAD 147.

The hardware elements depicted in computer 101 are not intended to be exhaustive, but rather are representative to highlight essential components required by the present invention. For instance, computer 101 may include alternate memory storage devices such as magnetic cassettes, digital versatile disks (DVDs), Bernoulli cartridges, and the like. These and other variations are intended to be within the spirit and scope of the present invention.

Figure 2:
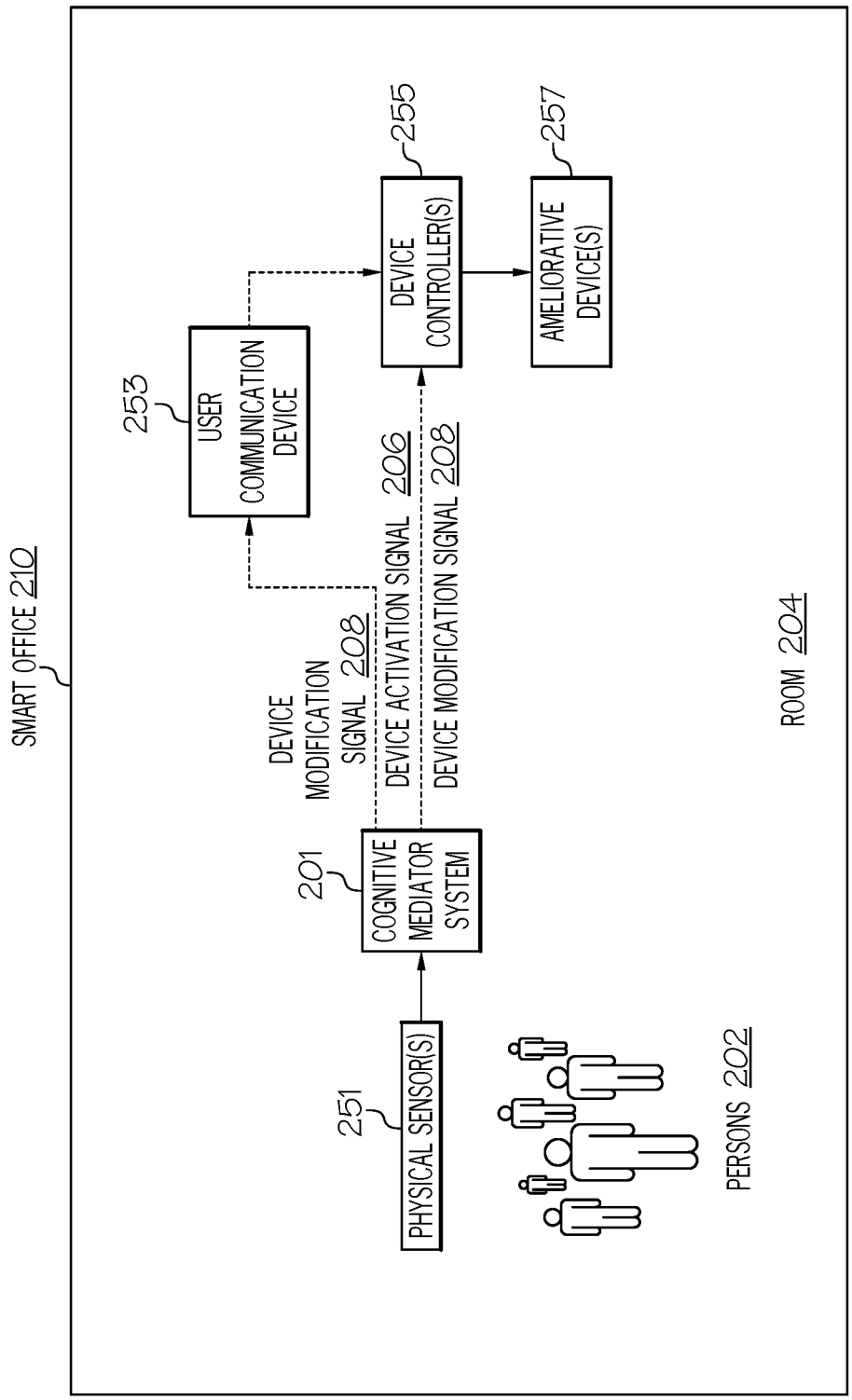
FIG. 2 illustrates a relationship among a cognitive mediator system, physical sensors, device controllers, and ameliorative device(s) in accordance with one or more embodiments of the present invention.

With reference now to FIG. 2, an exemplary relationship among a cognitive mediator system 201 (analogous to computer 101 shown in FIG. 1), physical sensors(s) 251 (analogous to physical sensor(s) 151 shown in FIG. 1), a user communication device 253 (analogous to user communication device 153 shown in FIG. 1), device controller(s) 255 (analogous to device controller(s) 155 shown in FIG. 1), and/or ameliorative device(s) 257 (analogous to ameliorative device(s) 157 shown in FIG. 1) is shown in accordance with one or more embodiments of the present invention.

Assume now that a group of two or more persons 202 (or alternatively, a single person) are in a physical space, such as room 204. In one or more embodiments of the present invention, room 204 is part of a smart office 210, which contains multiple physical devices that are able to communicate with and/or control each other as an Internet of Things (IoT). That is, this IoT is made up of devices that can receive signals, messages, instructions, sensor readings, etc. from other devices in the IoT, in order to enable a coordinated control and operation of the devices in the IoT.

Assume now that physical sensor(s) 251 detect 1) a state of the persons 202 and/or a state of the room 204. That is, one or more of the physical sensor(s) 251 may be cameras, microphones, biometric sensors, etc. that detect the movement, speech, temperature, etc. of the persons 202. Furthermore, one or more of the physical sensor(s) 251 may be cameras, microphones, thermometers, etc. that detect ambient noise in room 204, the room temperature of room 204, etc. The physical sensor(s) 251 send their respective sensors readings to cognitive mediator system 201, which uses these sensor readings to generate a device activation signal 206 and/or a device modification signal 208, in order to control the amelioration device(s) 257 as described herein.

The cognitive mediator system 201 is thus able to infer the cognitive state S of the persons 202 (e.g. distressed, tired, teething, in pain, upset, etc.), a context C of the persons 202 (e.g. they are in a meeting, are together in a family setting, are yelling, quiet, or crying, etc.), and an activity pattern P (including new behaviors) of the persons 202, where S, C, and P are all based on the sensors in the environment that show the time of day, the temperature and humidity of the room, the social setting, any crying, speech, conversations, and vocalization patterns of the persons in the room.

Once the cognitive mediator system 201 has ascertained the state of the persons 202 and/or the room 204, it will directly (or indirectly, via a user communication device 253) send a device activation signal 206 to the device controller(s) 255, which control the operation of ameliorative device(s) 257 that ameliorate the detrimental state of the persons 202.

Assume that the detrimental state of the persons 202 is that they are in a highly agitated state. As such, activating ameliorative device(s) 257 will cause the persons 202 to calm down.

For example, if one or more of the ameliorative device(s) 257 is an audio player (e.g., a CD player, an MP3 player, etc.), then the device activation signal will turn on the audio player, causing it to play soothing music (i.e., music that is known to have a calming effect on the persons 202), a recording of an appropriate adage (e.g., a poem or other writing that is known to have a calming effect on the persons 202), etc. If the ameliorative device(s) 257 is a video player (e.g., a DVD player, a video streaming device, etc.), then the device activation signal will turn on the video player, causing it to display a soothing nature scene, a person speaking in a calming voice, etc. All of these audio/visual recordings have been predetermined to have a calming effect on the particular persons (or type of persons) that make up persons 202.

In an embodiment of the present invention, the ameliorative device(s) 257 are devices that control the environment of room 204. For example, if the cognitive mediator system 201 determines that the persons 202 are in a high state of agitation, then the device controller(s) 255 may turn on an air conditioner (ameliorative device(s) 257) within room 204 by issuing the device activation signal 206, lower the temperature of the air conditioner by issuing the device modification signal 208, etc.

In an embodiment of the present invention, if the cognitive mediator system 201 determines that the persons 202 are in a high state of agitation, then the device controller(s) 255 may turn off lights (ameliorative device(s) 257) within 204 by issuing the device activation signal 206, lower the brightness of the lights by issuing the device modification signal 208, etc.

In an embodiment of the present invention, other actions may be performed by the cognitive mediator system 201 and/or the device controller(s) 255 that do not directly control the environment of room 204 or ameliorate the emotions of the persons 202. For example, assume that one of the persons 202 was scheduled to pick up a passenger (e.g., a family member) or an object (e.g., groceries), but was distracted by the hostilities of the group of persons 202. Assume further that a self-driving vehicle (i.e., an SDV that is able to drive from one location to another location in a fully autonomous mode without any human control inputs) is directed by a wireless signal from the device controller(s) 255 to the SDV (ameliorative device(s) 257) to pick up the person/cargo that the person from persons 202 was scheduled to pick up. Thus, that person's detrimental state is a combination of 1) being in a verbal altercation and 2) forgetting or otherwise being unable to pick up the person/cargo. Directing the SDV to pick up this person/cargo will therefore ameliorate the detrimental state of that person.

In an embodiment of the present invention, the device activation signal 206 and/or the device modification signal 208 are not sent from the cognition mediator system 201 directly to the device controller(s) 255, but rather are sent to a user communication device 253 (e.g., a cell phone), which may be used by one of the persons 202. When the device activation signal 206 and/or the device modification signal 208 is sent to the user communication device 253, the device controller(s) 255 initially have not directed the ameliorative device(s) 257 to do anything, since the device controller(s) 255 have not yet received the device activation signal 206 and/or the device modification signal 208. Furthermore, the user communication device 253 cannot directly control the ameliorative device(s) 257, since there is not direct communication between the user communication device 253 and the ameliorative device(s) 257. However, assume that a display (visual or aural) on the user communication device 253 is able to alert the user that the device activation signal 206 and/or the device modification signal 208 has been sent to the user communication device 253.

Assume now that user communication device 253 and device controller(s) 255 are able to communicate via a short-range signal (e.g., a signal with a range of less than 10'). As such, when the user communication device 253 comes within some predefined/technology based distance (e.g., 10') of the device controller(s) 255, it will send the device activation signal 206 and/or the device modification signal 208 to the device controller(s) 255, thus overcoming the network-centric problem of the user of the user communication device 253 not knowing that the ameliorative device(s) 257 has been activated. Furthermore, and more specifically, the user communication device 253 will activate an application (e.g., PCAD 147 shown in FIG. 1 and residing within device controller(s) 255) that controls the ameliorative device(s) 257), with the knowledge of the user of user communication device 253. For example, a first message may be displayed on user communication device 253 stating that it has received the device activation signal 206 and/or the device modification signal 208, followed by a second message displayed on the user communication device 253 stating that PCAD 147 has been activated within the device controller(s) 255, in order to activate/modify the ameliorative device(s) 257. This feature is especially useful if the user communication device 253 is not initially within room 204, since it will encourage/prompt the user to enter the room 204, in order to be close to the device controller(s) 255 and the persons 202.

As described above, the ameliorative device(s) 257 may be a self-driving vehicle (SDV). Thus, FIG. 3 provides additional details of one or more embodiments of an SDV 357 (which may be one of the ameliorative device(s) 257 shown in FIG. 2).

Figure 3:
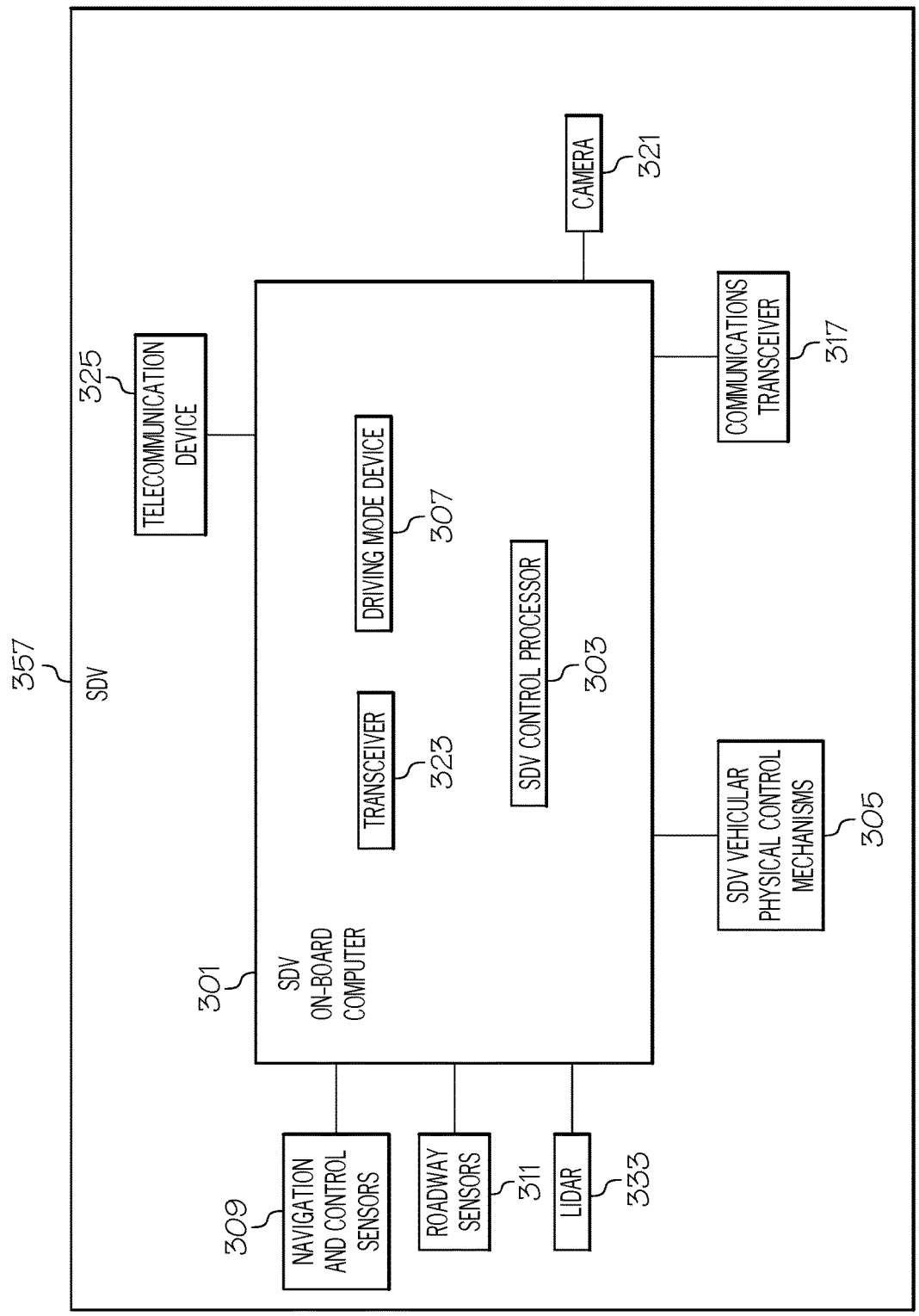
FIG. 3 depicts details of an exemplary self-driving vehicle (SDV) that may be utilized in one or more embodiments of the present invention.

As shown in FIG. 3, SDV 357 has an SDV on-board computer 301 (analogous to computer 101 shown in FIG. 1) that controls operations of the SDV 357. According to directives from a driving mode device 307, the SDV 357 can be selectively operated in manual mode ("human driven") or autonomous ("fully computer controlled") mode. In some embodiments, driving mode device 307 is a dedicated hardware device that selectively directs the SDV on-board computer 301 to operate the SDV 357 in one of the autonomous modes or in the manual mode.

While in autonomous mode, SDV 357 operates without the input of a human driver, such that the engine, steering mechanism, braking system, horn, signals, etc. are controlled by the SDV control processor 303, which is now under the control of the SDV on-board computer 301. That is, by the SDV on-board computer 301 processing inputs taken from navigation and control sensors 309 and the driving mode device 307 (indicating that the SDV 357 is to be controlled autonomously), then driver inputs to the SDV control processor 303 and/or SDV vehicular physical control mechanisms 305 are no longer needed.

As just mentioned, the SDV on-board computer 301 uses outputs from navigation and control sensors 309 to control the SDV 357. Navigation and control sensors 309 include hardware sensors that 1) determine the location of the SDV 357; 2) sense other cars and/or obstacles and/or physical structures around SDV 357; 3) measure the speed and direction of the SDV 357; and 4) provide any other inputs needed to safely control the movement of the SDV 357.

With respect to the feature of 1) determining the location of the SDV 357, this can be achieved through the use of a positioning system such as positioning system 151 shown in FIG. 1. Positioning system 151 may use a global positioning system (GPS), which uses space-based satellites that provide positioning signals that are triangulated by a GPS receiver to determine a 3-D geophysical position of the SDV 357. Positioning system 151 may also use, either alone or in conjunction with a GPS system, physical movement sensors such as accelerometers (which measure acceleration of a vehicle in any direction), speedometers (which measure the instantaneous speed of a vehicle), airflow meters (which measure the flow of air around a vehicle), etc. Such physical movement sensors may incorporate the use of semiconductor strain gauges, electromechanical gauges that take readings from drivetrain rotations, barometric sensors, etc.

With respect to the feature of 2) sensing other cars and/or obstacles and/or physical structures around SDV 357, the positioning system 151 may use radar or other electromagnetic energy that is emitted from an electromagnetic radiation transmitter (e.g., transceiver 323 shown in FIG. 3), bounced off a physical structure (e.g., another car), and then received by an electromagnetic radiation receiver (e.g., transceiver 323). An exemplary positioning system within SDV 357 is a Light Detection and Ranging (LIDAR) (e.g., LIDAR 333 shown in FIG. 3) or Laser Detection and Ranging (LADAR) system that measures the time it takes to receive back the emitted electromagnetic radiation (e.g., light), and/or evaluates a Doppler shift (i.e., a change in frequency to the electromagnetic radiation that is caused by the relative movement of the SDV 357 to objects being interrogated by the electromagnetic radiation) in the received electromagnetic radiation from when it was transmitted, the presence and location of other physical objects can be ascertained by the SDV on-board computer 301. In one or more embodiments, different SDVs are able to directly communicate with one another in order to let one another know their relative positions. That is, a first SDV may transmit its GPS coordinates to a second SDV (and vice versa), thus allowing the first SDV and the second SDV to know the current real-time GPS-coordinate location of the other SDV.

With respect to the feature of 3) measuring the speed and direction of the SDV 357, this can be accomplished by taking readings from an on-board speedometer (not depicted) on the SDV 357 and/or detecting movements to the steering mechanism (also not depicted) on the SDV 357 and/or a positioning system (e.g., a global positioning system—GPS, not shown).

With respect to the feature of 4) providing any other inputs needed to safely control the movement of the SDV 357, such inputs include, but are not limited to, control signals to activate a horn, turning indicators, flashing emergency lights, etc. on the SDV 357.

In one or more embodiments of the present invention, SDV 357 includes roadway sensors 311 that are coupled to the SDV 357. Roadway sensors 311 may include sensors that are able to detect the amount of water, snow, ice, etc. on a roadway (e.g., using cameras, heat sensors, moisture sensors, thermometers, etc.). Roadway sensors 311 also include sensors that are able to detect "rough" roadways (e.g., roadways having potholes, poorly maintained pavement, no paving, etc.) using cameras, vibration sensors, etc.

In one or more embodiments of the present invention, a camera 321 can be movably trained on roadway, in order to provide photographic images of conditions on the roadway upon which the SDV 357 is traveling.

In one or more embodiments of the present invention, camera 321 can be trained on a location (e.g., pickup location or delivery location) and/or a person (e.g., a passenger) of SDV 357. This feature provides a record of a passenger or cargo being picked up at the pickup location.

In one or more embodiments of the present invention, also within SDV 357 is a communications transceiver 317, which is able to receive and transmit electronic communication signals (e.g., RF messages) from and to other communications transceivers found in other vehicles, servers, monitoring computers, etc.

In one or more embodiments of the present invention, also within SDV 357 is a telecommunication device 325 (e.g., a smart phone, a cell phone, a laptop computer, etc.), which may be connected (e.g., via a short-range radio connection) to the SDV on-board computer 301.

Figure 4:
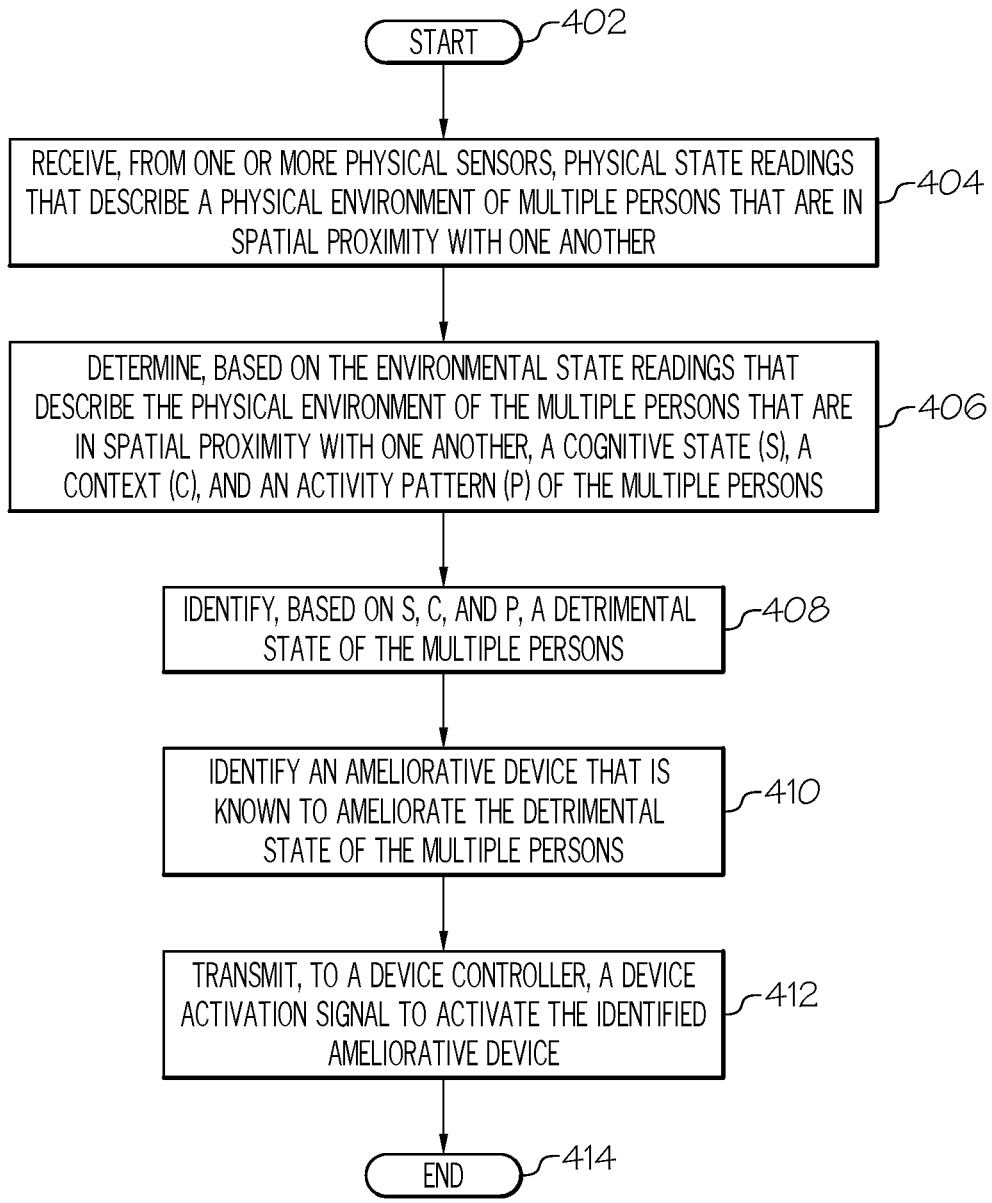
FIG. 4 is a high-level flow chart of one or more steps performed by one or more processors and/or other hardware devices in accordance with one or more embodiments of the present invention.

With reference now to FIG. 4, a high-level flow chart of one or more steps performed by one or more processors and/or other hardware devices in accordance with one or more embodiments of the present invention is presented.

After initiator block 402, a cognitive mediator system (e.g., cognitive mediator system 201 shown in FIG. 2) receives, from one or more physical sensors (e.g., physical sensor(s) 253 shown in FIG. 2), physical state readings that describe a physical environment of multiple persons that are in spatial proximity with one another (e.g., persons 202 shown in FIG. 2), as described in block 404. That is, these multiple persons are all within a same area, such as within room 204 shown in FIG. 2, and the physical sensors sense the environment of the room 204, which includes the presence and appearance of the persons 202 within the room 204.

As described in block 406, the cognitive mediator system, based on the physical state readings that describe the physical environment of the multiple persons that are in spatial proximity with one another, then determines: a cognitive state (S) for the multiple persons that are in spatial proximity with one another (e.g., if the persons 202 are happy, angry, etc.); a context (C) for the multiple persons that are in spatial proximity with one another (e.g., the physical setting that is room 204 in which the multiple persons are located); and an activity pattern (P) of the multiple persons, where P describes behaviors (such as yelling, crying, etc.) of the multiple persons that are in spatial proximity with one another.

As described in block 408, the cognitive mediator system, based on S, C, and P, identifies a detrimental state of the multiple persons. For example, the cognitive mediator system determines that the persons 202 are arguing.

As described in block 410, the cognitive mediator system identifies an ameliorative device (e.g., one or more of ameliorative device(s) 257 shown in FIG. 2) that is known to ameliorate the detrimental state of the multiple persons. That is, based on the context C and activity pattern P of the persons 202, the cognitive mediator system 201 is able to determine that they are angry with one another (cognitive state S). In the past, however, a particular ameliorative device has proven to be effective in calming down one or more of this particular group of persons 202. As such, the cognitive mediator system 201 will assume that this particular ameliorative device will again being able to calm down persons 202 if it is activated and/or adjusted as described in FIG. 2.

As described in block 412, the cognitive mediator system transmits, to a device controller (e.g., one or more of the device controller(s) 255 shown in FIG. 2), a device activation signal (e.g., device activation signal 206) to activate the identified ameliorative device, thus ameliorating the detrimental state (e.g., anger) of one or more of the persons 202.

The flow-chart shown in FIG. 4 ends at terminator block 414.

In an embodiment of the present invention, the cognitive mediator system transmits, to the device controller, a device modification signal (e.g., device modification signal 208 shown in FIG. 2) to modify the identified ameliorative device. For example, this device modification signal may direct the device controller to turn down the volume on a music player, dim the lights, etc. within room 204.

In an embodiment of the present invention, the cognitive mediator system includes a rule-based heuristic engine that utilizes and modifies a set of rules to identify the ameliorative device based on user profiles of the multiple persons. For example, assume that user profiles (stored within cognitive mediator system 201) of persons 202 shows that they have a tendency to become agitated if exposed to loud music and bright lights. An initial rule may be to turn down music when the persons 202 are detected as being angry. However, when the cognitive mediator system 201 retrieves the user profiles for the multiple persons 202, it "learns" (heuristically) that the set of rules for persons 202 should also include the rule that these persons, if angry, should not be subjected to bright lights. As such, the ameliorative device (a dim light) is identified as the appropriate ameliorative device for the persons 202.

In an embodiment of the present invention, the cognitive mediator system includes one or more custom learning models that identify the ameliorative device based on user profiles of the multiple persons. That is, the cognitive mediator system "learns" heuristically as just described, but no rules are involved. Rather, the cognitive mediator system learns by trial and error what works (i.e., which ameliorative device is effective) for reducing the detrimental state (e.g., anger) of the persons 202.

In an embodiment of the present invention, the cognitive mediator system predicts a future occurrence of the detrimental state in the multiple persons based on S, C, P, and a past history of occurrences of the detrimental state in the multiple persons. That is, the cognitive mediator system recognizes the current state, context, and activity pattern of the persons. If they have a history of getting angry with one another when this state, context, and activity pattern have occurred in the past, then the cognitive mediator system will predict that the detrimental state (e. g., getting angry) is going to recur, even if it has not done so yet. Thus, based on this prediction and in an effort to thwart the detrimental state before it occurs, the cognitive mediator system will preemptively direct the device controller to activate the identified ameliorative device before the future occurrence of the detrimental state occurs in the multiple persons.

In an embodiment of the present invention, the cognitive mediator system transmits the device activation signal 206 to a user communication device (e.g., user communication device 253 shown in FIG. 2). As described above, in an embodiment of the present invention the user communication device is in wireless communication with the device controller, and the user communication device wirelessly transmits the device activation signal to the device controller in response to the user communication device coming within a predefined distance of the device controller. Thus, the device controller is inactive until the user communication device is within the predefined distance of the device controller.

In an embodiment of the present invention, the identified ameliorative device is part of an Internet of Things (IoT) within a smart room, and the smart room contains the IoT that are activated by one or more device controllers. That is, the ameliorative device(s) 257 shown in FIG. 2 are able to communicate with one another (i.e., an IoT), such that they are able to directly coordinate their activities. For example, if the cognitive mediator system 201 tells a first lamp (one of the ameliorative device(s) 257 within the room 204) to dim, then that first lamp can tell a second lamp (another of the ameliorative device(s) 257 within the room 204) to also dim, as both lamps are part of the IoT.

In an embodiment of the present invention, the identified ameliorative device is a self-driving vehicle (SDV). As described above, the cognitive mediator system 201, upon determining that one of the persons 202 that is in a detrimental state (e.g., is arguing with other persons from persons 202), transmits an instruction to the SDV to transport a passenger or cargo, which that person was scheduled to transport at the time of the argument.

The present invention assumes that permission has been granted by persons 202 to perform the processes described herein. For example, in an embodiment of the present invention, all persons from persons 202 must send permission (e.g., from their cell phones) to cognitive mediator system 201 to perform the steps presented herein. That is, persons 202 may have an expectation of safety while in room 202, and thus may expressly assent to being in an environment that is controlled by cognitive mediator system 201.

The present invention may be implemented in one or more embodiments using cloud computing. Nonetheless, it is understood in advance that although this disclosure includes a detailed description on cloud computing, implementation of the teachings recited herein is not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
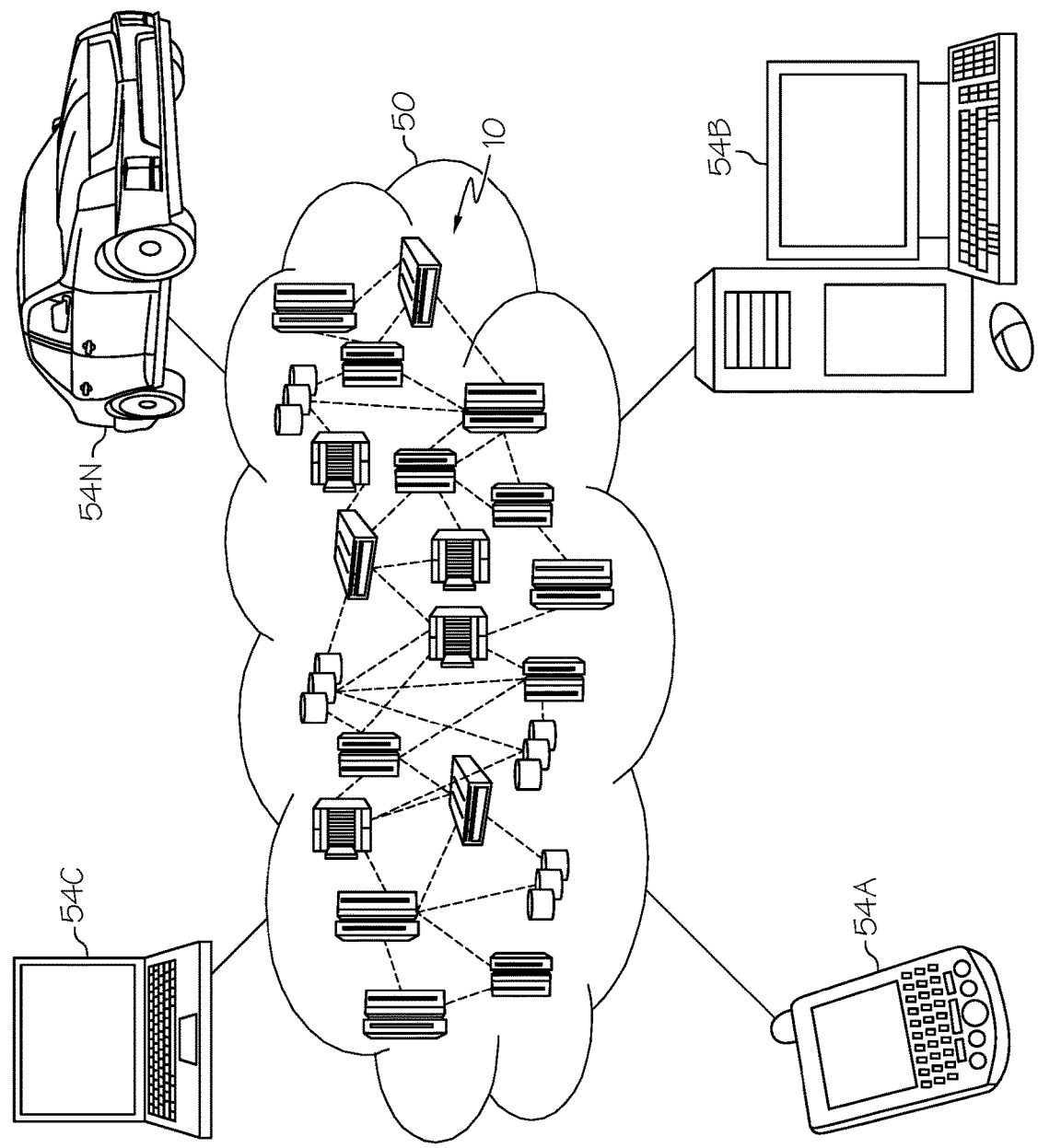
FIG. 5 depicts a cloud computing environment according to one or more embodiments of the present invention.

Referring now to FIG. 5, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-54N shown in FIG. 5 are intended to be illustrative only and that computing nodes 10 and cloud computing environment 50 can communicate with any type of computerized device over any type of network and/or network addressable connection (e.g., using a web browser).

Figure 6:
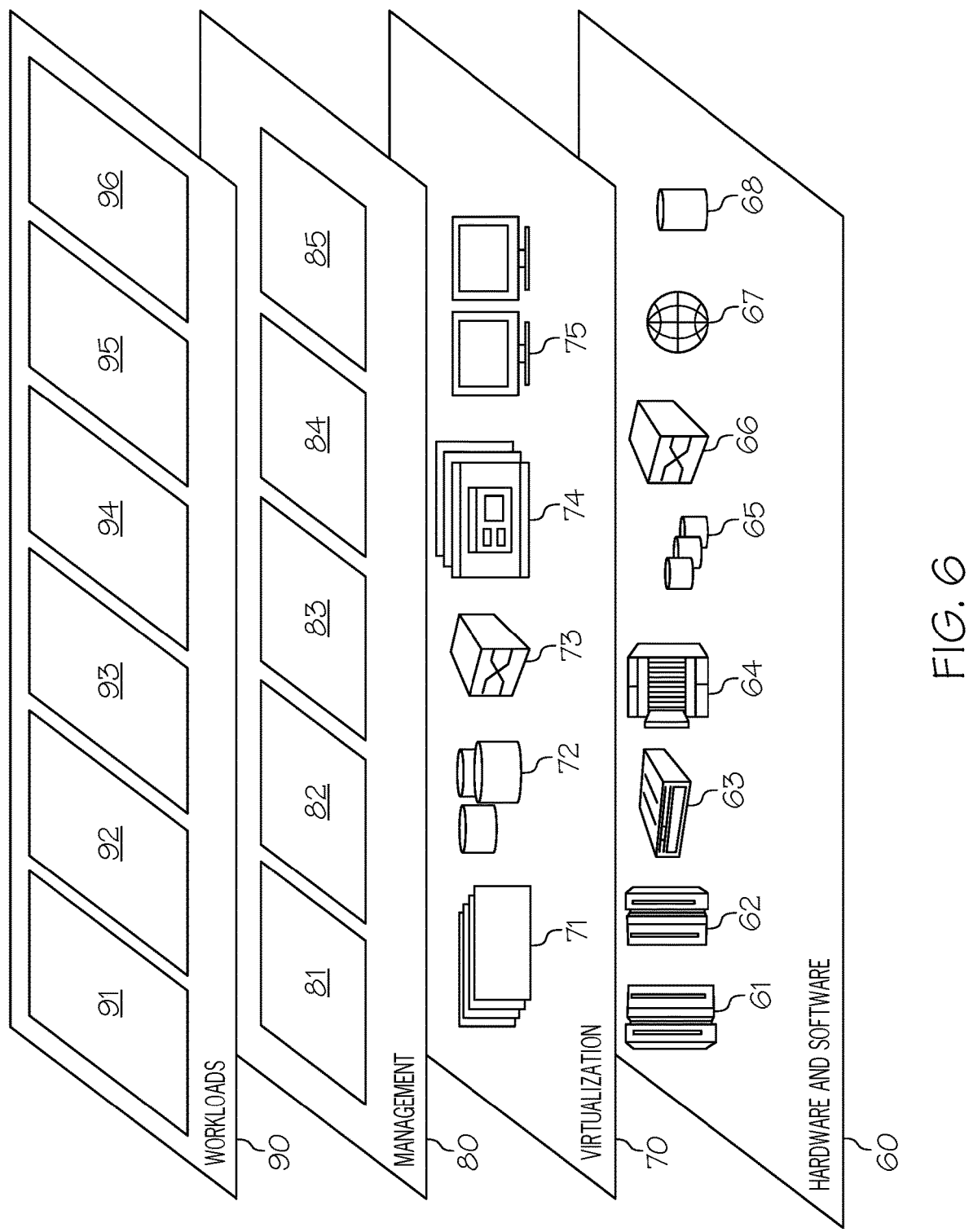
FIG. 6 depicts abstraction model layers of a cloud computer environment according to one or more embodiments of the present invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and ameliorative device control processing 96, which performs one or more of the features of the present invention described herein.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

Any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A method comprising:
  receiving, from one or more physical sensors, state readings that describe a physical environment of multiple persons that are in spatial proximity with one another;
  determining, based on the physical state readings that describe the physical environment of the multiple persons that are in spatial proximity with one another,
    a context for the multiple persons that are in spatial proximity with one another, wherein the context describes a physical setting in which the multiple persons are located;

identifying, based on the context that describes the physical setting in which the multiple persons are located, a state of the multiple persons; and transmitting, to a device controller of a self-driving vehicle (SDV), a device activation signal to activate the SDV, wherein the device activation signal directs the SDV to transport cargo that one of the multiple persons was previously scheduled to transport, wherein the device activation signal is transmitted to the device controller of the SDV via a user communication device, wherein the user communication device is in wireless communication with the device controller of the SDV, wherein the user communication device wirelessly transmits the device activation signal to the device controller of the SDV in response to the user communication device coming within a predefined distance of the device controller of the SDV, and wherein the device controller of the SDV is inactive until the user communication device is within the predefined distance of the device controller of the SDV.

2. The method of claim 1, further comprising:
transmitting, to the device controller of the SDV, a device modification signal to modify the SDV.

3. The method of claim 1, further comprising:
modifying, by a rule-based heuristic engine, a set of rules to identify the SDV based on user profiles of the multiple persons.

4. The method of claim 1, further comprising:
predicting, by one or more processors, a future occurrence of the state of the multiple persons based on the context that describes the physical setting in which the multiple persons are located S, C, P, and a past history of occurrences of the state of the multiple persons; and
directing, by one or more processors, the device controller of the SDV to activate the SDV before the future occurrence of the state occurs in the multiple persons.

5. The method of claim 1, wherein the method is implemented in a cloud environment.

6. A computer program product for controlling a self-driving vehicle (SDV), the computer program product comprising a non-transitory computer readable storage device having program instructions embodied therewith, the program instructions readable and executable by a computer to perform a method comprising:
receiving, from one or more physical sensors, state readings that describe a physical environment of multiple persons that are in spatial proximity with one another;
determining, based on the physical state readings that describe the physical environment of the multiple persons that are in spatial proximity with one another,
a context for the multiple persons that are in spatial proximity with one another, wherein the context describes a physical setting in which the multiple persons are located;
identifying, based on the context that describes the physical setting in which the multiple persons are located, a state of the multiple persons; and
transmitting, to a device controller of a self-driving vehicle (SDV), a device activation signal to activate the SDV, wherein the device activation signal directs the SDV to transport cargo that one of the multiple persons was previously scheduled to transport, wherein the device activation signal is transmitted to the device controller of the SDV via a user communication device, wherein the user communication device is in wireless communication with the device controller of the SDV, wherein the user communication device wirelessly transmits the device activation signal to the device controller of the SDV in response to the user communication device coming within a predefined distance of the device controller of the SDV, and wherein the device controller of the SDV is inactive until the user communication device is within the predefined distance of the device controller of the SDV.

7. The computer program product of claim 6, wherein the method further comprises:
modifying, by a rule-based heuristic engine, a set of rules to identify the SDV based on user profiles of the multiple persons.

8. The computer program product of claim 6, wherein the method further comprises:
predicting a future occurrence of the state of the multiple persons based on the context that describes the physical setting in which the multiple persons are located and a past history of occurrences of the state of the multiple persons; and
directing, by the one or more processors, the device controller of the SDV to activate the SDV before the future occurrence of the state occurs in the multiple persons.

9. The computer program product of claim 8, wherein the program instructions are provided as a service in a cloud environment.

10. A computer system comprising one or more processors, one or more computer readable memories, and one or more computer readable storage mediums, and program instructions stored on at least one of the one or more computer readable storage mediums for execution by at least one of the one or more processors via at least one of the one or more computer readable memories, the stored program instructions comprising:
program instructions to receive, from one or more physical sensors, physical state readings that describe a physical environment of multiple persons that are in spatial proximity with one another;
program instructions to determine, based on the physical state readings that describe the physical environment of the multiple persons that are in spatial proximity with one another,
a context for the multiple persons that are in spatial proximity with one another, wherein the context describes a physical setting in which the multiple persons are located;
program instructions to identify, based on the context that describes the physical setting in which the multiple persons are located, a state of the multiple persons; and
program instructions to transmit, to a device controller of a self-driving vehicle (SDV), a device activation signal to activate the SDV, wherein the device activation signal directs the SDV to transport cargo that one of the multiple persons was previously scheduled to transport, wherein the device activation signal is transmitted to the device controller of the SDV via a user communication device, wherein the user communication device is in wireless communication with the device controller of the SDV, wherein the user communication device wirelessly transmits the device activation signal to the device controller of the SDV in response to the user communication device coming within a predefined distance of the device controller of the SDV, and wherein the device controller of the SDV is inactive until the user communication device is within the predefined distance of the device controller of the SDV.

11. The computer system of claim 10, further comprising:
program instructions to predict a future occurrence of the state of the multiple persons based on the context that describes the physical setting in which the multiple persons are located and a past history of occurrences of the state of the multiple persons; and
program instructions to direct the device controller of the SDV to activate the SDV before the future occurrence of the state occurs in the multiple persons.

12. The computer system of claim 10, wherein the stored program instructions are executed as a service in a cloud environment.

* * * * *